US009040077B2

(12) United States Patent
Terashi et al.

(10) Patent No.: US 9,040,077 B2
(45) Date of Patent: May 26, 2015

(54) PATCH AND PATCH PREPARATION

(75) Inventors: Sachiko Terashi, Ibaraki (JP); Akinori Hanatani, Ibaraki (JP); Hitoshi Akemi, Ibaraki (JP); Yoshihiro Iwao, Ibaraki (JP)

(73) Assignee: NITTO DENKO CORPORATION, Osaka (JP)

( * ) Notice: Subject to any disclaimer, the term of this patent is extended or adjusted under 35 U.S.C. 154(b) by 193 days.

(21) Appl. No.: 12/656,700

(22) Filed: Feb. 12, 2010

(65) Prior Publication Data

US 2010/0203108 A1 Aug. 12, 2010

(30) Foreign Application Priority Data

Feb. 10, 2009 (JP) ................. 2009-028903

(51) Int. Cl.
*A61L 15/16* (2006.01)
*A61K 9/70* (2006.01)
*A61F 13/00* (2006.01)

(52) U.S. Cl.
CPC ....... *A61K 9/703* (2013.01); *A61F 2013/00651* (2013.01); *A61K 9/7061* (2013.01)

(58) Field of Classification Search
USPC .......................................... 424/447
See application file for complete search history.

(56) References Cited

U.S. PATENT DOCUMENTS

| 3,528,416 | A * | 9/1970 | Chamberlain | 128/888 |
| 4,619,253 | A | 10/1986 | Anhauser et al. | |
| 5,374,429 | A * | 12/1994 | Kinoshita et al. | 424/448 |
| 6,177,482 | B1 | 1/2001 | Cinelli et al. | |
| 6,555,730 | B1 | 4/2003 | Albrod et al. | |
| 2004/0265361 | A1* | 12/2004 | Kuniya et al. | 424/445 |
| 2008/0299183 | A1 | 12/2008 | Ameyama et al. | |
| 2009/0246264 | A1 | 10/2009 | Andersen et al. | |

FOREIGN PATENT DOCUMENTS

| CN | 1572330 | 2/2005 |
| CN | 101313896 | 12/2008 |
| EP | 0 144 891 | 6/1985 |
| EP | 0 569 862 | 11/1993 |
| EP | 1 491 219 | 12/2004 |
| EP | 1 716 850 | 11/2006 |
| JP | 46-13598 | 5/1971 |
| JP | 49-112900 | 2/1974 |
| JP | 60-168450 | 8/1985 |
| JP | 5-309128 | 11/1993 |
| JP | 11-9623 | 1/1999 |
| JP | 2000-109427 | 4/2000 |
| JP | 2000-297033 | 10/2000 |
| JP | 1189675 | 11/2003 |
| JP | 2005-13316 | 1/2005 |
| JP | 2005-224981 | 8/2005 |
| JP | 2006-207092 | 8/2006 |
| JP | 2006-288887 | 10/2006 |
| JP | 1340351 | 9/2008 |
| JP | 3145046 | 9/2008 |
| JP | 2009-22730 | 2/2009 |
| WO | 2007/065427 | 6/2007 |
| WO | WO 2007065427 A1 * | 6/2007 ............... A61K 9/70 |

OTHER PUBLICATIONS

European Search Report issued May 20, 2011 in corresponding European Patent Application No. 10153152.3.
Ryan Donnelly et al., "Potential of Photodynamic Therapy in Treatment of Fungal Infections of the Mouth. Design and Characterisation of a Mucoadhesive Patch Containing Toluidine Blue O", Journal of Photochemistry and Photobiology B: Biology, Elsevier Science S.A., Basel, CH, vol. 86, No. 1, Dec. 6, 2006, pp. 59-69, XP005794973.
A. Wokovich et al., "Evaluation of Substrates for 90° Peel Adhesion—A Collaborative Study. II. Transdermal Drug Delivery Systems", Journal of Biomedical Materials Research, Part B: Applied Biomaterials, vol. 88B, No. 1, 2008, pp. 61-65, XP002636248.
Chinese Office Action issued Jul. 4, 2012 corresponding to Application No. 201010116576.6 with English translation.
Chinese Office Action issued Dec. 13, 2012 in Chinese Application No. 201010116576.6, with English translation thereof.
Japanese Submission of Publication, etc. filed Jan. 16, 2013 in Japanese Application No. 2010-25498, with English translation thereof.
"Percutaneously absorptive-type bronchodilator, Hokunalin® tape", pp. 1-4, Sep. 2004 (with attached explanation).
Press release relating to "indication of 'Hokunalin' on the tape surface of 'Hokunalin® tape' (tulobuterol patch), which is an adhesive-type, long-acting bronchodilator first in the world, for the purpose of securing 'safety in use'", May 2006.
Document related to percutaneous analgesic and antiphlogistic agent, Pestec® Tape, Oct. 2005 (with attached explanation).
Document related to percutaneous analgesic and antiphlogistic agent, Proarisin® Tape, Dec. 2008 (with attached explanation).
JPO Notification of provision of information by the Submission of Publication, etc. dated Feb. 12, 2013.
Search Report issued Feb. 14, 2014 in corresponding European Application No. 10 153 152.3.
Office Action issued Aug. 13, 2013 in corresponding Japanese Application No. 2010-025498, with English translation thereof.
Decision on Rejection issued Feb. 13, 2014 in corresponding Chinese Application No. 201010116576.6, with English language translation.
Observations in relation to European Application No. 10 153 152.3, dated Oct. 28, 2013.
Notice for Reasons for Refusal issued Oct. 28, 2014 in corresponding Japanese Application No. 2014-020319, with English translation thereof.
Office Action issued Dec. 24, 2014 in corresponding Japenese Application No. 2010-25498, with English language translation thereof.
English translation of JP 2000-297033 published Oct. 24, 2000.
English translation of JP 2000-109427 published Apr. 18, 2000.

* cited by examiner

*Primary Examiner* — Michael B Pallay
(74) *Attorney, Agent, or Firm* — Wenderoth, Lind & Ponack, L.L.P.

(57) ABSTRACT

The present invention provides to a patch and a patch preparation having low stretchability, which can be continuously adhered to the skin for a long time without undesirable detachment and marked falling off from the skin due to various factors during adhesion, and specifically provides a low stretchable patch and a patch preparation containing a support and an adhesive layer formed on one surface of the support, wherein a ratio P of the total length W (mm) of curved sections of a planar outer shape of the patch to the total length S (mm) of straight-line sections of the planar outer shape of the patch (W/S) is not more than 1.22, and, when the curved sections are approximated by a circular arc, the radius R (mm) of the circular arc is not less than 0.5 mm.

8 Claims, 5 Drawing Sheets

PRIOR ART

PATCH AND PATCH PREPARATION

TECHNICAL FIELD OF THE INVENTION

The present invention relates to a patch and a patch preparation having a support and an adhesive layer. More particularly, the present invention relates to a patch and a patch preparation having low stretchability, which can be continuously adhered to the skin for a long time without undesirable detachment and marked falling off from the skin due to various factors during adhesion.

BACKGROUND OF THE INVENTION

Patch preparations having a rectangular outer shape are conventionally known. However, the patch may be undesirably detached and markedly fall off from the skin due to various factors during adhesion. As references dealing with, the problems of undesirable detachment, for example, the following references can be mentioned.

JP-A-2000-109427 (patent document 1) discloses a patch having a water-containing adhesive layer formed on one surface of a support and a support having an atypical outer shape, and teaches that such patch shows good adhesiveness even on a curved skin surface and is not easily detached therefrom.

In addition, JP-A-2000-297033 (patent document 2) discloses a patch having a water-containing adhesive layer formed on one surface of a support, and a rectangular outer shape with round corners. It is taught therein that such roundness prevents easy detachment.

For even such patches, however, when the patch is adhered for a long time to the skin covered with clothes, the patch may be detached due to the friction with the clothes. In addition, the patches of the above-mentioned references have high stretchability, and a detach operation necessary when detachment is desired is relatively troublesome. The references do not teach any solving means for providing a patch with low stretchability wherein the detachment from the skin is sufficiently suppressed even when it is adhered for a long time to the skin covered with clothes.

PRIOR ART REFERENCES patent document 1: JP-A-2000-109427
patent document 2: JP-A-2000-297033

SUMMARY OF THE INVENTION

The present invention has been made in view of such situation, and the problem to be solved is provision of a patch and a patch preparation having low stretchability, which can be continuously adhered to the skin for a long time without undesirable detachment and marked falling off from the skin due to various factors during adhesion.

The present inventors have worked on the problem that a low stretchable patch cannot avoid undesirable detachment even when the outer shape thereof have round corners, and unexpectedly found that an undesirable detachment of the patch can be sufficiently suppressed by ensuring the straight-line section of its outer shape, which resulted in the completion of the present invention.

Accordingly, the present invention provides
(1) A low stretchable patch comprising a support and an adhesive layer formed on one surface of the support, wherein a ratio P of the total length W (mm) of curved sections of a planar outer shape of the patch to the total length S (mm) of straight-line sections of the planar outer shape of the patch (W/S) is not more than 1.22, and, when the curved sections are approximated by a circular arc, the radius R (mm) of the circular arc is not less than 0.5 mm.
(2) The patch according to (1), having a 5% modulus of not less than 0.5(N).
(3) The patch according to (1), wherein the outermost layer surface of the support has a coefficient of static friction of not more than 1.0.
(4) The patch according to (1), wherein the adhesive layer is non-aqueous.
(5) A patch preparation comprising the patch according to any of (1)-(4), wherein the adhesive layer contains a drug.

According to the present invention, the patch has low stretchability, and the outer shape of the patch has a total length of the straight-line sections and a total length of the curved sections at a predetermined ratio. As a result, irrespective of low stretchability, undesirable detachment of the patch does not occur easily even when it is adhered to the skin under clothes for a long time. In addition, since the patch has low stretchability, it has a certain level of rigidity, can be adhered to the skin with ease, and can be detached easily when so desired. Since such patch permits strict control of the timing of adhesion and detachment, it can be widely used for a patch, as well as particularly superior for a patch preparation intended to strictly control the dose of a drug.

A preferable embodiment of the present invention is shown in the following, wherein detailed explanations and particular examples are only for exemplification purposes, and do not limit the scope of the present invention. The explanation of the preferable embodiment below is only for exemplification purposes, and does not limit the scope of the present invention, application thereof and use thereof.

Figure 1:
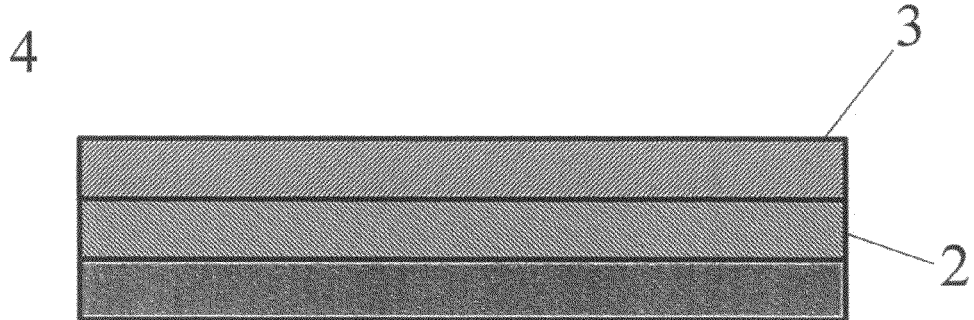
FIG. 1 is a schematic sectional view of an embodiment of the patch of the present invention, wherein 1 is a support, 2 is an adhesive layer, 3 is a release liner, and 4 is a patch.

FIG. 1 is a schematic sectional view of an embodiment of the patch of the present invention, wherein a release liner 3 is included for the purpose of explanation. In the following description, unless interpreted differently in the context, the "patch" of the present invention means a laminate of a support and an adhesive layer.

Figure 2:
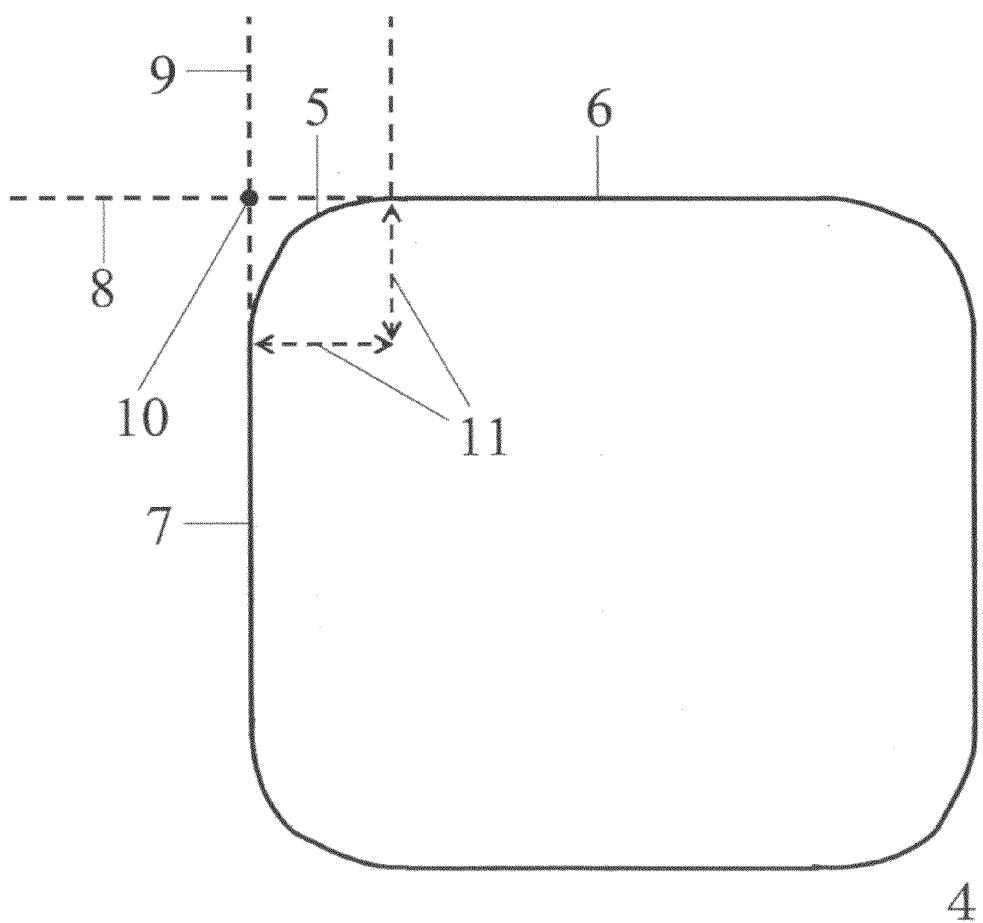
FIG. 2 is a schematic plane view of an embodiment of the patch of the present invention, wherein 4 is a patch, 5 is a curved section, 6 and 7 are straight-line sections, 8 and 9 are extensions, 10 is the point where extensions cross, and 11 is radius R.
Figure 3:
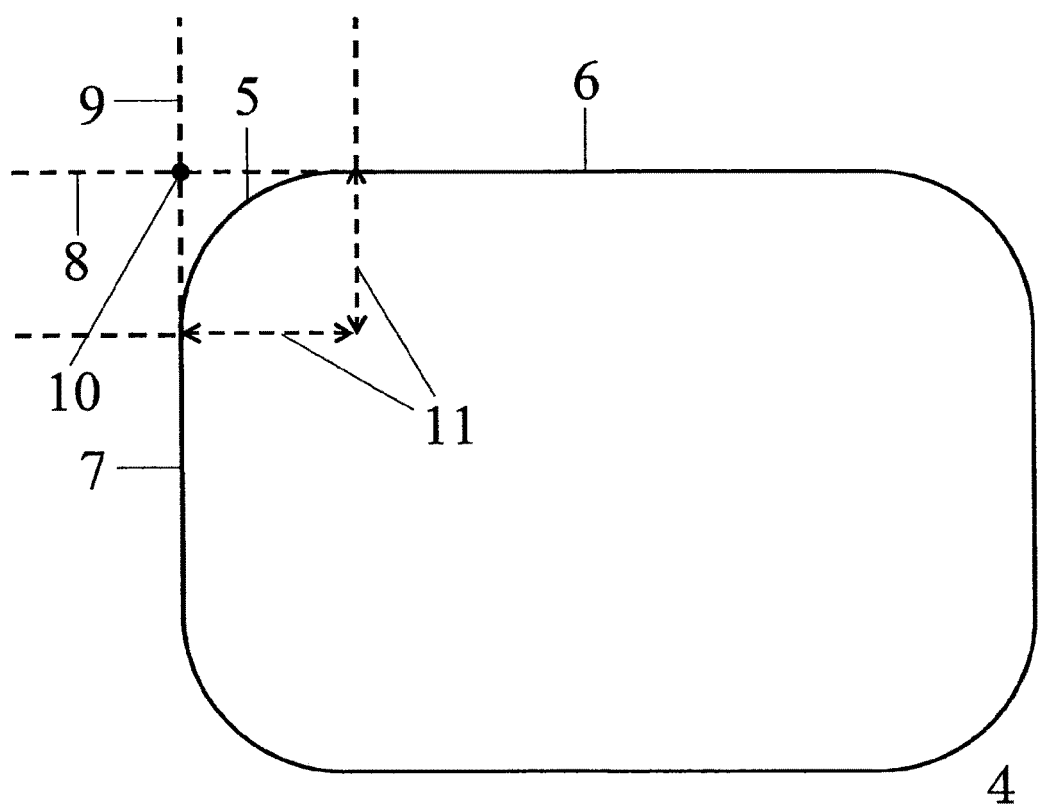
FIG. 3 is a schematic plane view of another embodiment of the patch of the present invention, wherein 4 is a patch, 5 is a curved section, 6 and 7 are straight-line sections, 8 and 9 are extensions, 10 is the point where extensions cross, and 11 is radius R.
Figure 4:
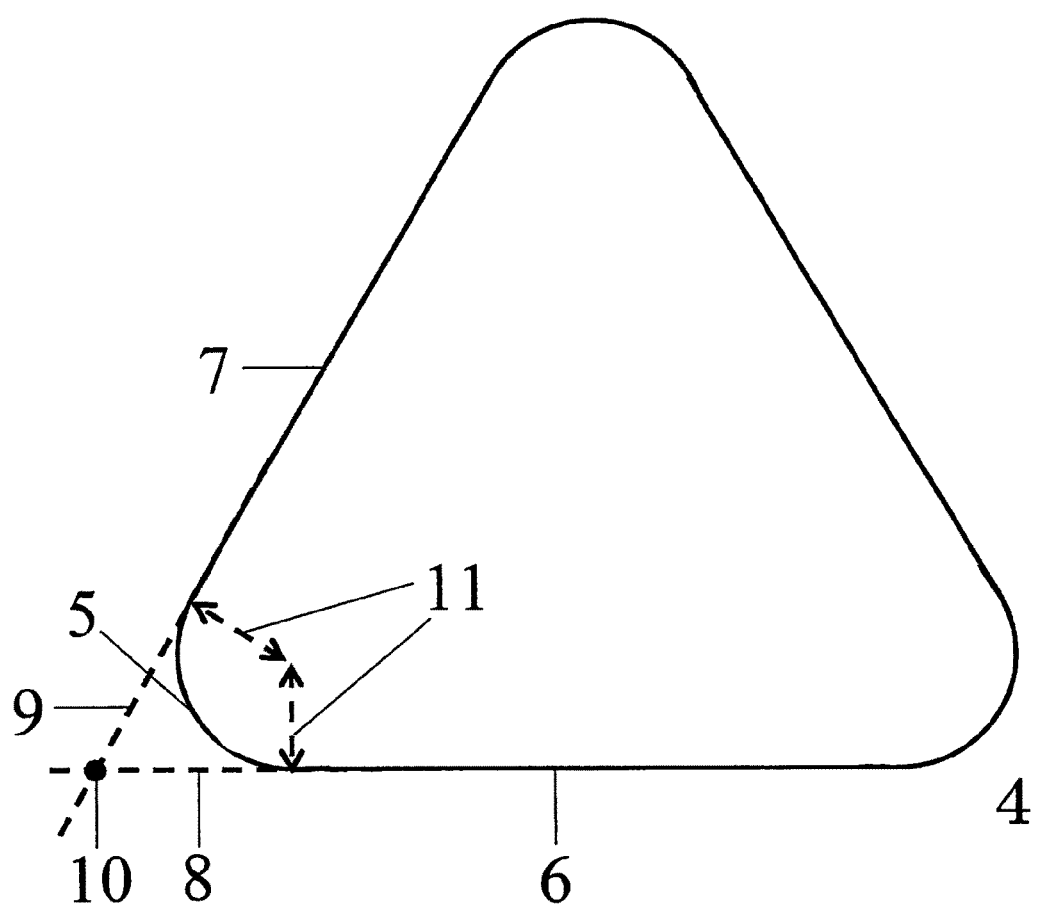
FIG. 4 is a schematic plane view of still another embodiment of the patch of the present invention, wherein 4 is a patch, 5 is a curved section, 6 and 7 are straight-line sections, 8 and 9 are extensions, 10 is the point where extensions cross, and 11 is radius R.
Figure 5:
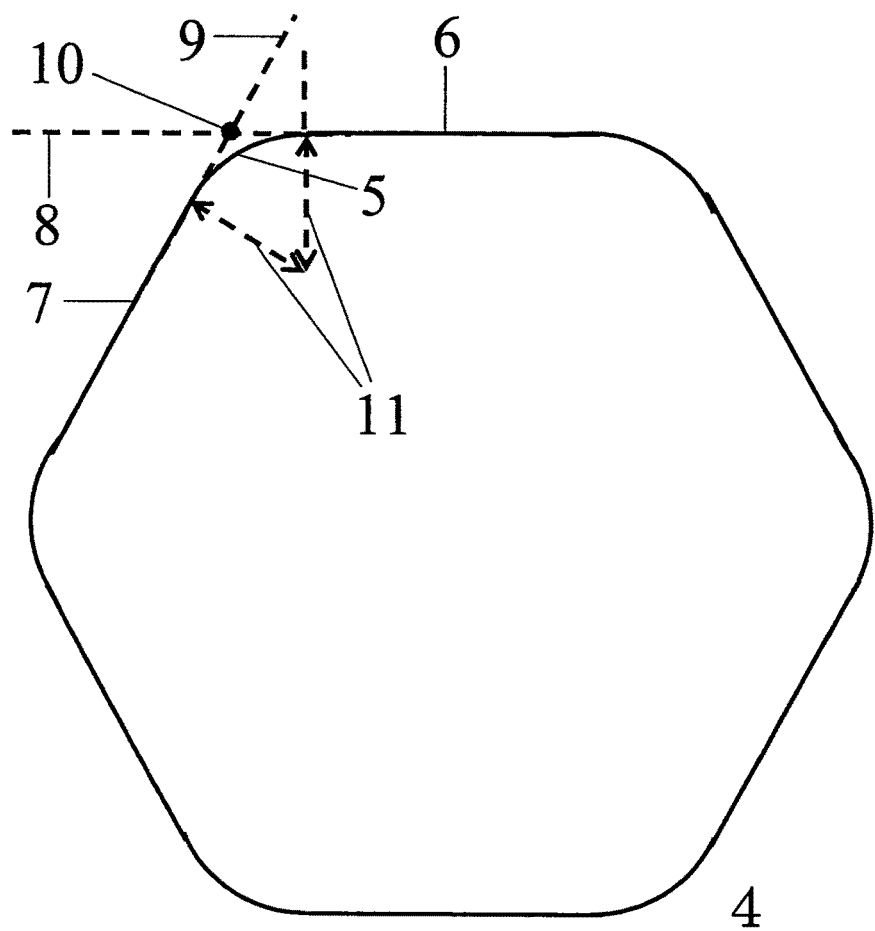
FIG. 5 is a schematic plane view of still another embodiment of the patch of the present invention, wherein 4 is a patch, 5 is a curved section, 6 and 7 are straight-line sections, 8 and 9 are extensions, 10 is the point where extensions cross, and 11 is radius R.

Referring to FIG. 2 and the planar outer shape of the patch of the present invention, when adjacent two straight-line sections 6 and 7 sandwiching a curved section 5 of the planar outer shape are extended and a point 10 at which two extensions cross is assumed to be a corner of the outer shape of the patch, the outer shape forms a polygon. In the present specification, polygon includes a shape in a strict sense which has corners, as well as the above-mentioned shape (e.g., quadrangle (for example, square, rectangle), triangle, pentagon, hexagon etc.). The embodiment of FIG. 2 is a square. In the embodiment of FIG. 3, the planar outer shape of the patch is a rectangle. In the embodiment of FIG. 4, the planar outer shape of the patch is a triangle. In the embodiment of FIG. 5, the planar outer shape of the patch is a hexagon. In the present invention, the planar outer shape of the patch is preferably a rectangle from the aspects of utilization efficiency of materials and handling of the patch.

Figure 6:
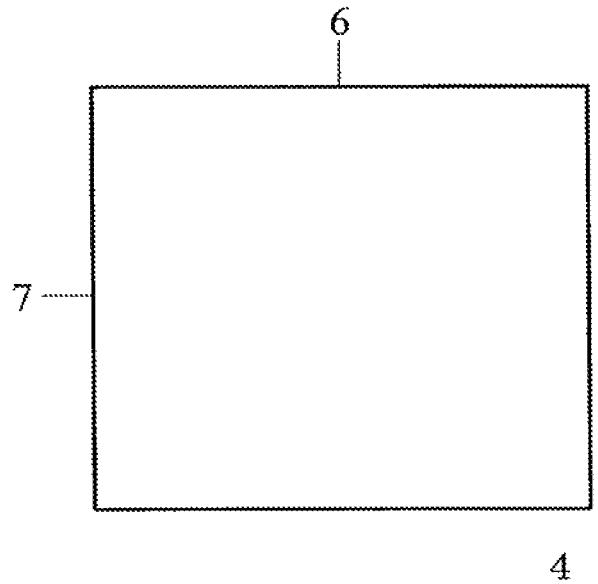
FIG. 6 is a schematic plane view of an embodiment of a conventional patch, wherein 4 is a patch, and 6 and 7 are straight-line sections.
Figure 7:
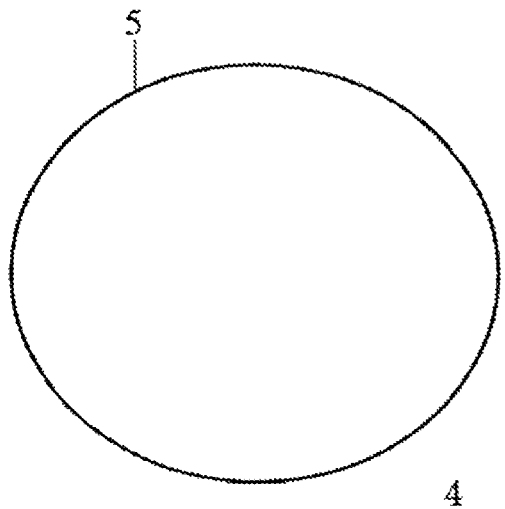
FIG. 7 is a schematic plane view of another embodiment of a conventional patch, wherein 4 is a patch, and 5 is a curved section.

The patch of the present invention is explained by referring to FIG. 2 again. As a result of the studies of the present inventors, it has been found that when a low stretchable patch is adhered to the skin and the patch is frictioned with clothes, the patch tends to start detaching from a non-straight-line section of the outer shape thereof, i.e., a corner or a curved section. In FIG. 6, the conventional patch has a corner. Such patch tends to start detaching from a corner during adhesion to the skin. In FIG. 7, the conventional patch does not have a corner in the planar outer shape and is constituted with curved sections alone. Such patch tends to start detaching from any curved section during adhesion to the skin. In other words, as is conventionally understood, even when a patch has round corners, detachment of the patch cannot be suppressed sufficiently, contrary to the prediction. On the other hand, it has also been found that even when a straight-line section of the outer shape of the patch is frictioned with clothes, the straight-line section is more resistant to the detachment than a corner or a curved section, and the detachment less often starts from a straight-line section.

Reference is made to FIG. 2 again, which shows an embodiment of the patch of the present invention. Based on such finding, when a patch is under a friction force in any direction from the clothes, it is considered useful to design the patch such that the straight-line section of the outer shape bears the highest possible friction force. From such aspects, a ratio P of the total length W (mm) of curved sections of a planar outer shape of the patch to the total length S (mm) of straight-line sections of the planar outer shape of the patch (W/S) needs to be not more than 1.22. That is, in the present invention, when P exceeds 1.22, namely, when the ratio of the total length of the curved sections to the total length of straight-line sections is higher than the above-mentioned value, curved section is frictioned with clothes more frequently during adhesion of the patch, the patch tends to start detaching early from the curved sections. As a result, the produced detached part gradually increases by repeated friction with the clothes, and finally, the patch falls off from the skin at undesirable timing. P is not particularly limited as long as it is not more than 1.22. Since complete absence of a curved section conversely facilitates detachment, P is preferably higher than 0, more preferably higher than 0.01.

On the other hand, when the curved sections 5 are approximated by a circular arc, and the radius R 11 (mm) of the circular arc is too small, since the curved section is entangled with the fiber of the clothes, the stress from the clothes is concentrated on the curved section, and the patch tends to start detaching early from the curved section 5. From such aspect, when the curved sections 5 are approximated by a circular arc, the radius R (mm) of the circular arc needs to be 0.5 mm or above. To exhibit sufficient effect of the invention, R (mm) is preferably not less than 0.75 mm, more preferably not less than 1.00 mm. The radius of the circular arc of all the curved sections of the outer shape of the patch is preferably not less than 0.5 mm. While R is not particularly limited as long as it is not less than 0.5 mm, since P tends to increase as R becomes higher, it is preferably smaller than 40, more preferably smaller than 20, most preferably not more than 19.5.

In the present invention, the patch needs to be low stretchable. When the patch is low stretchable, the patch acquires rigidity, and easily adhered to the skin. Typically, therefore, the stretchability of the patch can be achieved by the selection of a support.

In the present invention, the "low stretchability" means a 5% modulus of not less than 0.5 N, preferably not less than 1.0 N. In the present specification, 5% modulus means the force [N] necessary for expanding a test piece by 5% while affording a width of 10 mm and at least a chuck interval of 10 mm. To avoid doubt, the test piece does not have a release liner. The influence of the size of the test piece on the 5% modulus is neglectably small as long as the size is within the size range of conventional patches. When a sufficiently large test piece is obtained, a patch test piece of width 25 mm, length 100 mm is cut out and the 5% modulus thereof is measured according to the test method described in JIS Z 0237-2000.

The stretchability of the patch can be adjusted by a method known to those of ordinary skill in the art. Since the support can be an important factor to define the stretchability of the patch since the stretchability of a flexible adhesive layer can be almost ignored.

While such a support is not particularly limited, it desirably has a certain level of rigidity to enable easy adhesion of a patch to the skin.

Examples of the support include single films such as resin films (e.g., polyester, nylon, Saran (registered trade mark), polyethylene, polypropylene, polyvinyl chloride, ethylene-ethyl acrylate copolymer, polytetrafluoroethylene, Surlyn (registered trade mark) and the like), metal foil and the like; laminate films thereof, and the like. The thickness of the support is generally 10-500 μm, preferably 10-300 μm.

Among these, to achieve a good adhesion force (anchoring force) between a support and an adhesive layer, the support is preferably a laminate film of a non-porous plastic film and a porous film produced from the above-mentioned materials. In this case, an adhesive layer is preferably formed on the porous film side. On the other hand, for the texture and good appearance of the patch, the porous film surface is desirably exposed. For this end, the adhesive layer is preferably formed on the plastic film side.

Specific examples of the porous film include paper, woven fabric, non-woven fabric, knitted fabric, mechanically perforated sheet and the like, which can be laminated on the aforementioned film. In view of the low stretchability, paper and non-woven fabric are particularly preferable from among those. To easily obtain a low stretchable support, the support preferably contains a resin film or a metal foil.

When a woven fabric or a non-woven fabric is used as a porous film, the fabric weight is 5-30 $g/m^2$, preferably 6-20 $g/m^2$.

The most preferable support in the present invention is a laminate film of a 1.5-6 μm thick polyester film (preferably, polyethylene terephthalate film) and a polyester (preferably, polyethylene terephthalate) non-woven fabric (fabric weight 6-12 g/m$^2$).

The thickness of the aforementioned support can be calculated by photographing the section of a support using a digital microscope manufactured by KEYENCE (VHX-600, with VH-100 lens, magnification ×200), measuring the thickness of the support in the image at 3 or more points using a digital microscope with a built-in image processing software, and taking the average.

Assuming that a patch is adhered to the skin and covered with the clothes, the coefficient of static friction of the surface of the outermost layer of the support is preferably 0.01 or more and 1.0 or less. The coefficient of static friction in such preferable range can be achieved by appropriately selecting the material of the elements constituting the support. When the coefficient of static friction is too high, the patch is easily detached due to the friction with the clothes. For a patch having a coefficient of static friction thereof of less than 0.01, the material thereof is difficult to select. The coefficient of static friction here is measured by the measurement method described in JIS P 8147-1994.

The adhesive to be used for an adhesive layer is not particularly limited, and examples include acrylic adhesive comprising an acrylic polymer; rubber adhesives such as styrene-diene-styrene block copolymer (e.g., styrene-isoprene-styrene block copolymer, styrene-butadiene-styrene block copolymer and the like), polyisoprene, polyisobutylene, polybutadiene and the like; silicone adhesives such as silicone rubber, dimethylsiloxane base, diphenylsiloxane base and the like; vinyl ether adhesives such as polyvinyl methylether, polyvinyl ethylether, polyvinyl isobutylether and the like; vinyl ester adhesives such as vinyl acetate-ethylene copolymer and the like; polyester adhesives comprising a carboxylic acid component such as dimethylterephthalate, dimethylisophthalate, dimethylphthalate and the like and a polyvalent alcohol component such as ethylene glycol and the like, and the like, which can be used alone or a mixture of two or more kinds thereof.

Among such adhesives, an acrylic adhesive, particularly an acrylic adhesive which can easily be crosslinked, is preferable. Such an acrylic adhesive layer can thereby retain a large amount of liquid component, which can provide a soft feeling with skin during adhesion to the skin. When the adhesive layer contains a drug, a rubber adhesive is preferable for ensuring the drug stability.

Examples of such an acrylic adhesive include an acrylic acid ester adhesive containing, as a main component, a polymer obtained by polymerization of (meth)acrylic acid $C_{2-18}$ alkyl ester as a polymerizable component. An acrylic acid ester adhesive using an acrylic acid as a copolymerizable component is preferable since adhesiveness to the human skin is fine, and an adhesive obtained by copolymerization of a mixture of 2-ethylhexyl acrylate as a (meth)acrylic acid alkyl ester and acrylic acid and N-vinyl-2-pyrrolidone at a weight ratio of 40-99.9:0.1-10:0-50 is preferable since adhesion and detachment can be repeated easily. When desired, these adhesives may be applied to physical crosslinking by irradiation such as ultraviolet irradiation, electron beam irradiation and the like, or chemical crosslinking treatment using an isocyanate compound such as trifunctional isocyanate and the like and various crosslinking agents such as organic peroxide, organic metal salt, metal alcoholate, metal chelate compound, multifunctional compound (multifunctional external crosslinking agent, or multifunctional internal crosslinkable monomer such as diacrylate, dimethacrylate and the like) and the like.

Examples of the rubber adhesive include a rubber adhesive comprising, as a main component, at least one kind of elastomer selected from polyisobutylene, polyisoprene and styrene-diene-styrene copolymer. Since high drug stability, and necessary adhesion force and cohesion force can be simultaneously afforded, an adhesive obtained by blending high molecular weight polyisobutylene having a viscosity average molecular weight of 500,000-5,500,000, and low molecular weight polyisobutylene having a viscosity average molecular weight of 10,000-200,000 at a weight ratio of 95:5-5:95 and, where necessary, adding a tackifier is preferable. In the present specification, the rubber adhesive means a rubber elastomer which is adhesive by itself, or an adhesive polymer composition comprising a rubber elastomer and a tackifier.

Examples of the tackifier include polybutenes, petroleum resin (e.g., aromatic petroleum resin, aliphatic petroleum resin), terpene resin, rosin resin, coumarone indene resin, styrene resin (e.g., styrene resin, α-methylstyrene), hydrogenated petroleum resin (e.g., alicyclic saturated hydrocarbon resin) and the like. Among these, polybutenes are preferable since drug preservation stability is improved. Tackifiers can be used in a combination of one or more kinds thereof.

The amount of the tackifier is preferably 30-90 wt %, more preferably 50-70 wt %, relative to the total weight of an adhesive. When the amount of the tackifier is less than 30 wt %, the tackiness is sometimes low, and when it exceeds 90 wt %, the adhesive layer becomes hard and the skin adhesiveness tends to decrease.

The thickness of the adhesive layer is generally 10-500 μm, preferably 10-300 μm. In the patch of the present invention, a release liner is preferably laminated on the adhesive face of the adhesive layer to protect the adhesive face until use.

From the aspects of skin adhesiveness, a non-aqueous adhesive layer is preferable. The non-aqueous adhesive layer here is not necessarily limited to one completely free of water, but includes those containing a slight amount of water derived from humidity in the air, skin and the like. To afford sufficient skin adhesiveness, a patch having an adhesive layer with a low water content is preferable, wherein the water content of the patch is preferably not more than 10 wt %, more preferably not more than 5 wt %, most preferably not more than 2 wt %. Here, the water content of a patch is a weight ratio of water contained in a patch after detachment of a release liner when present (weight ratio of water relative to the total weight of the patch) as measured according to the Karl Fischer coulometric titration method and, in the present specification, measured under the measurement conditions described in the below-mentioned Examples.

The release liner is not particularly limited as long as sufficiently light detachability can be secured and, for example, films of polyester, polyvinyl chloride, polyvinylidene chloride, polyethylene terephthalate and the like, paper such as high quality paper, glassine paper and the like, a laminate film of high quality paper or glassine paper and polyolefin, and the like, wherein the surface to be in contact with an adhesive layer is release-treated by applying silicone resin, fluororesin and the like, can be mentioned.

The thickness of the release liner is generally 10-200 μm, preferably 25-100 μm.

As the release liner for the present invention, a liner produced from a polyester (particularly, polyethylene terephthalate) resin is preferable in view of the barrier property and cost. In this case, moreover, a liner having a thickness of about 25-100 μm is more preferable from the aspects of handling property. While the planar outer shape of the release liner may be the same as that of the other parts of the patch (support and adhesive layer), it may protrude from the planar outer shape of the patch (support and adhesive layer) (i.e., dry edge) to suppress protrusion of the adhesive layer (i.e., glue extrusion).

When desired, the adhesive layer can contain a drug to form a skin patch preparation. The drug herein is not particularly limited, and a drug that can be administered to a mammal such as human and the like through the skin thereof, i.e., a transdermally absorbable drug, is preferable. Specific examples of such a drug include general anesthetics, hypnotic sedatives, antiepileptic drugs, antipyretic analgesic antiphlogistic drugs, anti-vertiginous drugs, psychoneurotic drugs, topical anesthetics, skeletal muscle relaxants, autonomic drugs, antiepileptic drugs, anti-Parkinsonian drugs, anti-histamine drugs, cardiac stimulants, drugs for arrhythmia, diuretic, hypotensive drug, vasoconstrictor, coronary vasodilator, peripheral vasodilators, arteriosclerosis drugs, drugs for circulatory organ, anapnoics, antitussive expectorant, hormone drugs, external drugs for mattery diseases, analgesic-antipruritic-styptic-antiphlogistic drugs, drugs for parasitic dermatic diseases, drugs for arrest of bleeding, gout treatment drugs, drugs for diabetes, anti-malignant tumor drugs for, antibiotic, chemical therapy drugs, narcotic, quit smoking aids, anti-Alzheimer's drug and the like.

While the content of the drug is not particularly limited as long as the effect of the transdermally absorbable drug is provided and the adhesive property of the adhesive is not impaired, it is preferably 0.1-60 wt %, more preferably 0.5-40 wt %, of the adhesive layer. When the content is less than 0.1 wt %, the treatment effect may be insufficient. When it is more than 60 wt %, skin irritation may be developed and economical disadvantage may be caused.

When desired, the patch preparation may contain various additives in, for example, an adhesive layer thereof. Examples of such additives include plasticizer, transdermal absorption promoter and the like, and various other additives, such as antioxidant and the like. From the aspects of compatibility with an adhesive, a hydrophobic component is preferable.

Plasticizer can adjust the adhesive force to the adhesion site by plasticizing an adhesive. Examples of the plasticizer include diisopropyladipate, diacetylsebacate and the like, and the plasticizers can be used in a combination of one or more kinds thereof.

As a transdermal absorption enhancer, a compound which has a function to improve solubility and diffusability of a drug in an adhesive layer and improve transdermal absorption of a drug and the like can be used.

Examples of such a transdermal absorption enhancer include a compound that mainly enhances dissolution property of a drug such as glycols (e.g., ethylene glycol, diethylene glycol, propylene glycol, triethylene glycol, polyethylene glycol, polypropylene glycol and the like), a compound that mainly enhances diffusability of a drug such as fats and oils (e.g., olive oil, castor oil, squalane, lanolin and the like) and the like.

In addition to the above, hydrocarbons such as liquid paraffin, various surfactants, ethoxylated stearyl alcohol, glycerol monoesters such as oleic acid monoglyceride, caprylic acid monoglyceride and lauryl acid monoglyceride, glycerol diester, glycerol triester and a mixture thereof, higher fatty acid esters such as ethyl laurate, isopropyl myristate, isotridecyl myristate, octyl palmitate, isopropyl palmitate, ethyl oleate and diisopropyl adipate, higher fatty acids such as oleic acid and caprylic acid, as well as N-methylpyrrolidone, 1,3-butanediol and the like.

EXAMPLES

The present invention is explained in detail in the following by referring to Examples, which are not to be construed as limitative. In the following, "parts" means parts by weight. In Tables 1 and 2, the values of curve (W) and straight line (S) were obtained by rounding the measured values, and the value of P was obtained by rounding a value obtained by calculation using the values of W and S before rounding.

(1) Preparation of Acrylic Adhesive Solution

Under an inert gas atmosphere, 2-ethylhexyl acrylate (75 parts), N-vinyl-2-pyrrolidone (22 parts), acrylic acid (3 parts) and azobisisobutyronitrile (0.2 part) were subjected to solution polymerization in ethyl acetate at 60° C. to give an acrylic adhesive solution (adhesive solid concentration: 28 wt %).

(2) Preparation of Polyisobutylene Adhesive Solution

High molecular weight polyisobutylene (viscosity average molecular weight 900000, 28.5 parts), low molecular weight polyisobutylene (viscosity average molecular weight 60000, 43 parts), polybutene (number average molecular weight 1400, 8.5 parts), and alicyclic petroleum resin (softening point 100° C., 20 parts) were dissolved in hexane to give a polyisobutylene adhesive solution (solid concentration 25%).

Example 1

An acrylic adhesive solution in an amount to set an adhesive solid content to 44 parts and isopropyl myristate (54 parts) were stirred in a container to give a uniform mixture. To this mixture was added ethylacetoacetate aluminum diisopropylate in the proportion of 0.4 part per 100 parts of the solid content of the acrylic adhesive solution, the viscosity was adjusted with ethyl acetate, the liquid was laminated on a PET film (75 μm-thick) as a release liner such that the thickness of the adhesive layer after drying was 200 μm, adhered to a non-woven fabric side of a support ((total) thickness 54 μm) consisting of 2 μm-thick polyethylene terephthalate (hereinafter to be indicated as "PET") film/PET non-woven fabric (fabric weight 12 g/m$^2$), and aged (crosslinking treatment of adhesive layer) at 70° C. for 48 hr. The laminated sheet after aging was cut such that, when adjacent two straight-line sections of the curved sections of the planar outer shape are extended and the point at which two extensions cross is assumed to be a corner of the outer shape of the patch, the outer shape of the patch formed a square, the length of the side of the square containing the extension was 63 mm, and the curved sections form a circular arc with a radius of 0.5 mm, whereby the patch of Example 1 was obtained. This is to be indicated that the patch of Example 1 was obtained by cutting into a square of length and width 63 mm (corner is a circular arc with radius 0.5 mm). The same applies to Examples 1-10 and Comparative Examples 1-10.

Example 2

A patch was obtained in the same manner as in Example 1 except that the laminated sheet after aging was cut such that the corner was a circular arc with radius of 1.0 mm.

Example 3

A patch was obtained in the same manner as in Example 1 except that the laminated sheet after aging was cut into length and width 63.5 mm (corner was a circular arc with radius 5 mm).

Example 4

A patch was obtained in the same manner as in Example 1 except that the laminated sheet after aging was cut into length and width 63.5 mm (corner was a circular arc with radius 10 mm).

Example 5

A patch was obtained in the same manner as in Example 1 except that the laminated sheet after aging was cut into length and width 64.5 mm (corner was a circular arc with radius 15 mm).

Example 6

A patch was obtained in the same manner as in Example 1 except that the laminated sheet after aging was cut into length and width 65.5 mm (corner was a circular arc with radius 19.5 mm).

Comparative Example 1

A patch was obtained in the same manner as in Example 1 except that the laminated sheet after aging was cut into length and width 63 mm (corner was not a circular arc).

Comparative Example 2

A patch was obtained in the same manner as in Example 1 except that the laminated sheet after aging was cut into length and width 65.5 mm (corner was a circular arc with radius 20 mm).

Comparative Example 3

A patch was obtained in the same manner as in Example 1 except that the laminated sheet after aging was cut into length and width 65.5 mm (corner was a circular arc with radius 20.5 mm).

Comparative Example 4

A patch was obtained in the same manner as in Example 1 except that the laminated sheet after aging was cut into length and width 69 mm (corner was a circular arc with radius 30 mm).

Comparative Example 5

A patch was obtained in the same manner as in Example 1 except that the laminated sheet after aging was cut into a circle with radius 35.7 mm.

Example 7

A polyisobutylene adhesive solution was laminated on a PET film (75 μm-thick) such that the thickness after drying was 20 μm, and dried to form an adhesive layer. This was adhered to a PET film surface side of a support ((total) thickness 71 μm) consisting of 6 μm-thick PET film/PET nonwoven fabric (fabric weight 20 g/m$^2$), and aged at 25° C. for 7 days.

The laminated sheet after aging was cut into length and width 16 mm (corner was a circular arc with radius 0.5 mm) to give the patch of Example 7.

Example 8

A patch was obtained in the same manner as in Example 7 except that the laminated sheet after aging was cut such that the corner was a circular arc with radius 1.0 mm.

Example 9

A patch was obtained in the same manner as in Example 7 except that the laminated sheet after aging was cut such that the corner was a circular arc with radius 2.4 mm.

Example 10

A patch was obtained in the same manner as in Example 7 except that the laminated sheet after aging was cut into length and width 16.5 mm (corner was a circular arc with radius 5 mm).

Comparative Example 6

A patch was obtained in the same manner as in Example 7 except that the laminated sheet after aging was cut into length and width 16 mm (corner was not a circular arc).

Comparative Example 7

A patch was obtained in the same manner as in Example 7 except that the laminated sheet after aging was cut into length and width 17 mm (corner was a circular arc with radius 6.7 mm).

Comparative Example 8

A patch was obtained in the same manner as in Example 7 except that the laminated sheet after aging was cut into a circle with radius 9 mm.

Comparative Example 9

A patch was obtained in the same manner as in Example 1 except that the support was a knitted fabric (thickness 565 μm) of stretchable polyester and the laminated sheet after aging was cut into a square with length and width 63.5 mm (corner was a circular arc with radius 5 mm).

Comparative Example 10

A patch was obtained in the same manner as in Example 1 except that the support was a knitted fabric (thickness 565 μm) of stretchable polyester and the laminated sheet after aging was cut into a square with length and width 16 mm (corner was a circular arc with radius 2.4 mm).

TABLE 1

| | area (mm²) | side length (mm) | R (mm) | curve (W) (mm) | straight-line (S) (mm) | P | 5% modulus (N) | coefficient of static friction | detached area vs patch area | peelability after adhesion |
|---|---|---|---|---|---|---|---|---|---|---|
| Comparative Example 1 | 3969 | 63 | 0.0 | 0 | 252 | 0 | length 20 width 11 | 0.16 | 53% | — |
| Example 1 | 3969 | 63 | 0.5 | 3 | 248 | 0.01 | | | 22% | — |
| Example 2 | 3968 | 63 | 1.0 | 6 | 244 | 0.03 | | | 18% | — |
| Example 3 | 4011 | 63.5 | 5 | 31 | 214 | 0.15 | | | 12% | ○ |
| Example 4 | 3946 | 63.5 | 10 | 63 | 174 | 0.36 | | | 24% | — |
| Example 5 | 3967 | 64.5 | 15 | 94 | 138 | 0.68 | | | 19% | — |
| Example 6 | 3963 | 65.5 | 19.5 | 122 | 106 | 1.16 | | | 29% | — |
| Comparative Example 2 | 3946 | 65.5 | 20 | 126 | 102 | 1.23 | | | 40% | — |
| Comparative Example 3 | 3929 | 65.5 | 20.5 | 129 | 98 | 1.31 | | | 43% | — |
| Comparative Example 4 | 3987 | 69 | 30 | 188 | 36 | 5.23 | | | 56% | — |
| Comparative Example 5 | 4002 | 71.4 | 35.7 | 224 | 0 | | | | 64% | — |
| Comparative Example 6 | 256 | 16 | 0 | 0 | 64 | 0 | length 23 width 44 | 0.52 | 43% | — |
| Example 7 | 256 | 16 | 0.5 | 3 | 60 | 0.05 | | | 21% | — |
| Example 8 | 256 | 16 | 1.0 | 6 | 56 | 0.11 | | | 19% | — |
| Example 9 | 251 | 16 | 2.4 | 15 | 44.8 | 0.34 | | | 18% | ○ |
| Example 10 | 251 | 16.5 | 5.0 | 31 | 26 | 1.21 | | | 23% | — |
| Comparative Example 7 | 250 | 17 | 6.7 | 42 | 14.4 | 2.92 | | | 43% | — |
| Comparative Example 8 | 254 | 18 | 9.0 | 57 | 0 | | | | 68% | — |
| Comparative Example 9 | 4011 | 63.5 | 5 | 31 | 214 | 0.15 | length 0.05 | 1.03 | — | X |
| Comparative Example 10 | 251 | 16 | 2.4 | 15 | 45 | 0.34 | width 0.15 | | — | X |

The water content of the patch was 1.0 wt % or less in all cases.

Production Example Containing a Drug

Examples 11-13, Comparative Examples 11-14

An acrylic adhesive solution in an amount to set an adhesive solid content to 40 parts and isopropyl myristate (10 parts) and lidocain (50 parts) were stirred in a container to give a uniform mixture. To this mixture was added ethylacetoacetate aluminum diisopropylate in the proportion of 0.4 part per 100 parts of the solid content of the acrylic adhesive solution, the viscosity was adjusted with ethyl acetate, the liquid was applied to a PET film (75 μm-thick) as a release liner such that the thickness after drying was 60 μm, and dried to give an adhesive layer. The adhesive layer was adhered to a non-woven fabric side of a support consisting of 2 μm-thick PET film/PET non-woven fabric (fabric weight 8 g/m²), and aged (crosslinking treatment of adhesive layer) at 25° C. for 24 hr. The laminated sheet after aging was cut into rectangles shown in the Table, whereby the patches of Examples 11-13, Comparative Examples 11-14 were obtained.

Examples 14-17, Comparative Examples 15-18

To a polyisobutylene adhesive solution was added indomethacin such that the adhesive layer had an indomethacin content of 20%, they were mixed, sufficiently stirred, applied to a release liner such that the thickness after drying was 100 μm and dried to give an adhesive layer. The adhesive layer was adhered to a non-woven fabric side of a support consisting of 6 μm-thick PET film/PET non-woven fabric (fabric weight 8 g/m²), and aged (crosslinking treatment of adhesive layer) at 25° C. for 2 days. Further, the laminated sheet after aging was cut into rectangles shown in the Table, whereby the patches of Examples 14-17, Comparative Examples 15-18 were obtained.

The patch preparations (patches containing such drugs) showed an effect similar to that of a patch.

TABLE 2

| | area (mm²) | long side (mm) | short side (mm) | R (mm) | curve (W) (mm) | straight-line (S) (mm) | P |
|---|---|---|---|---|---|---|---|
| Comparative Example 11 | 80 | 10 | 8 | 0.0 | 0 | 36 | 0.00 |
| Example 11 | 80 | 10 | 8 | 0.5 | 3 | 32 | 0.10 |
| Example 12 | 79 | 10 | 8 | 1.0 | 6 | 28 | 0.22 |
| Example 13 | 81 | 10.5 | 8 | 2 | 13 | 21 | 0.60 |
| Comparative Example 12 | 82 | 10.5 | 8.5 | 3 | 19 | 14 | 1.35 |
| Comparative Example 13 | 81 | 10.5 | 9 | 4 | 25 | 7 | 3.59 |
| Comparative Example 14 | 78 | 10.5 | 9.5 | 5 | 31 | 0 | |
| Comparative Example 15 | 1500 | 50 | 30 | 0 | 0 | 160 | 0.00 |
| Example 14 | 1500 | 50 | 30 | 0.5 | 3 | 156 | 0.02 |
| Example 15 | 1499 | 50 | 30 | 1 | 6 | 152 | 0.04 |
| Example 16 | 1494 | 50.5 | 30 | 5.0 | 31 | 121 | 0.26 |
| Example 17 | 1495 | 51 | 31 | 10 | 63 | 84 | 0.75 |

TABLE 2-continued

|  | area (mm²) | long side (mm) | short side (mm) | R (mm) | curve (W) (mm) | straight-line (S) (mm) | P |
|---|---|---|---|---|---|---|---|
| Comparative Example 16 | 1487 | 52.5 | 32 | 15 | 94 | 49 | 1.92 |
| Comparative Example 17 | 1492 | 54 | 34 | 20.0 | 126 | 16 | 7.85 |
| Comparative Example 18 | 1509 | 55 | 35 | 22.0 | 138 | 4 | |

Note: With respect to the curved section in the planar outer shape, when adjacent two straight-line sections are extended and the point at which two extensions cross is assumed to be a corner of the outer shape of the patch, the outer shape of the patch forms a rectangle having a long side and a short side. The lengths of the long side and short side of the rectangle containing the extensions are shown in the Table.

(Test Method)

5% modulus

5% modulus was measured according to the test method described in JIS Z 0237-2000. The test piece used was a patch with width 25 mm, length 100 mm.

Coefficient of Static Friction

Coefficient of static friction was measured according to the test method described in JIS P 8147-1994.

Adhesion Test

Ten patches each of the above-mentioned Examples 1-10 and Comparative Examples 1-8 were prepared. Each patch of respective Examples was adhered to the chest or back of 30 persons, and they led a normal life. At 4 days after adhesion, the detached area relative to the patch area was recorded.

Ten patches each of the above-mentioned Examples 3 and 9, and Comparative Examples 9 and 10 were prepared. Each patch of respective Examples was adhered to the chest or back of 10 persons, and they led a normal life. After adhesion for 4 days, those easily detached were marked with 0, and those difficult to detach were marked with x.

The drug-containing patches of Examples 11-17 and Comparative Examples 11-18 are also subjected to an adhesion test, and the detached area relative to the patch area and peelability after adhesion are evaluated. Consequently, results similar to those of a patch without a drug are obtained.

Water Content Percentage

Under an environment of temperature 23±2° C. and relative humidity 40±5% RH, a patch having a release liner was punched into 7.5 cm² to give a test piece. Then, a release liner was removed from the test piece and the piece was placed in a water evaporation apparatus. The test piece was heated at 140° C. in the apparatus, the water developed thereby was introduced into a titration flask with nitrogen as a carrier, and the water content of the patch (wt %; weight ratio of water to the total weight of the patch) was measured by the Karl Fischer coulometric titration method.

The "side" in the description of the present Examples means a distance between the adjacent two corners when adjacent two straight-line sections are extended and the point at which two extensions cross is assumed to be a corner in the polygon in paragraph [0013]. The areas in the description of the present Examples are actual areas.

The explanation in the present invention is merely for exemplification purposes, and various modifications and changes to the particular embodiments shown without substantially departing from the teaching and advantages of the present invention are encompassed in the present invention. Such modifications should not be construed as those departing from the scope and spirit of the present invention.

This application is based on patent application No. 2009-028903 filed in Japan, the contents of which are hereby incorporated by reference.

EXPLANATION OF SYMBOLS 1 support
2 adhesive layer
3 release liner
4 patch
5 curved section
6 straight-line section
7 straight-line section
8 extension
9 extension
10 point at which adjacent two straight-line sections cross
11 radius R

The invention claimed is:

1. A low stretchable patch preparation, comprising:
a support and an adhesive layer formed on one surface of the support,
the adhesive layer containing a drug,
wherein the support is a laminate film of a non-porous plastic film which is a polyethylene terephthalate film and a porous film which is a polyethylene terephthalate non-woven fabric, and
the support and the adhesive layer have a planar outer shape comprising a plurality of straight-line sections and a plurality of curved sections,
wherein the adhesive layer is formed on the porous film,
wherein each straight-line section is connected to an adjacent straight-line section by a curved section,
wherein the plurality of straight-line sections have a total length S (mm), and the plurality of curved sections have a total length W (mm),
wherein the total length W (mm) of the curved sections of the planar outer shape of the patch to the total length S (mm) of the straight-line sections of the planar outer shape of the patch (W/S) is a ratio of greater than 0 but not more than 1.22,
wherein straight line extensions of the straight-line sections form a polygonal planar outer shape of the support and the adhesive layer,
wherein the curved sections are approximated by a circular arc, and
the radius R (mm) of the circular arc is not less than 0.5 mm.

2. The patch preparation according to claim 1, having a 5% modulus of not less than 0.5(N).

3. The patch preparation according to claim 1, wherein the outermost layer surface of the support has a coefficient of static friction of not more than 1.0.

4. The patch preparation according to claim 1, wherein the adhesive layer is non-aqueous.

5. The patch preparation according to claim 1, wherein the adhesive layer is laminated on the whole area of the one surface of the support porous film.

6. The patch preparation according to claim 1, wherein the porous film is laminated on the whole area of the non-porous plastic film.

7. The patch preparation according to claim 5, wherein the porous film is laminated on the whole area of the non-porous plastic film.

8. The patch preparation according to claim 1, wherein the support is a laminate film of a 1.5-6 µm thick polyethylene terephthalate film and a polyethylene terephthalate non-woven fabric of 6-12 g/m² fabric weight.

* * * * *